(12) United States Patent
Olweus et al.

(10) Patent No.: US 6,555,324 B1
(45) Date of Patent: Apr. 29, 2003

(54) METHOD TO DISTINGUISH HEMATOPOIETIC PROGENITOR CELLS

(75) Inventors: Johanna Olweus, Fremont, CA (US); Fridtjof Lund-Johansen, Fremont, CA (US); Leon Wmm Terstappen, Palo Alto, CA (US)

(73) Assignee: Becton Dickinson & Company, Franklin Lakes, NJ (US)

( * ) Notice: Subject to any disclaimer, the term of this patent is extended or adjusted under 35 U.S.C. 154(b) by 0 days.

(21) Appl. No.: 08/147,707

(22) Filed: Nov. 4, 1993

(51) Int. Cl.[7] ................ G01N 33/566; C12P 21/02; C07K 17/00
(52) U.S. Cl. ............... 435/7.24; 435/69.52; 530/351
(58) Field of Search ............... 435/7.24, 240.21, 435/240.2, 69.52; 530/351

(56) References Cited

PUBLICATIONS

Armitage et al. (1992) *Blood* 79: 1738–45*
Goodwin et al. (1990) *Cell* 60: 941–51.*
Kinniburgh et al. (1993) *Bone Marrow Transplant.* 12: 489–94.*
McClanahan et al. (1994) *Blood* 81: 2903–15.*
Terstappen et al. (1991) *Blood* 77: 1218–17.*

* cited by examiner

*Primary Examiner*—Gary L. Kunz
*Assistant Examiner*—Jegatheesan Seharaseyon
(74) *Attorney, Agent, or Firm*—Douglas A. Petry; David Schneck (57) ABSTRACT

The expression of various cell adhesion molecules and growth factor receptor was examined on human progenitor cells (i.e., $CD34^+/CD38^+$). Certain changes in the expression if one or more of these molecules and receptors correlates with the progression of cell from non-lineage committed to commitment to a specific lineage. Using one or more markers for these molecules and/or receptors in combination with markers for CD34 and CD38 will enable one to identify and isolate each of the different progenitor cell populations.

8 Claims, 11 Drawing Sheets

(9 of 11 Drawing Sheet(s) Filed in Color)

METHOD TO DISTINGUISH HEMATOPOIETIC PROGENITOR CELLS

FIELD OF THE INVENTION

This invention relates to the field of flow cytometry and the use of fluorescently labelled markers to distinguish between various cells types, and more particularly, this invention relates to a method for distinguishing among hematopoietic progenitor cells preferably by means of flow cytometry-wherein said cells are labelled with fluorescently labelled monoclonal antibodies.

BACKGROUND OF THE INVENTION

In U.S. Pat. No. 4,714,680, Civin described a population of pluripotent lympho-hematopoietic cells which were substantially free of mature lymphoid and myeloid cells. Civin also described an antigen, MY-10 and a monoclonal antibody (of the same name) thereto, which was present on these cells. These cells make up to about 1% of all cells in normal adult bone marrow, and generally comprise a mixture of totipotent, pluripotent stem cells and lineage committed progenitor cells with the latter cells predominating.

Since that time, MY-10 has been classified by the International Workshop on Human Leukocyte Antigens as falling with the cluster designated as "CD34. " Anti-CD34 monoclonal antibodies are commercially available from a number of sources including Becton Dickinson Immunocytometry Systems, San Jose, Calif. ("BDIS").

Given that most of the cells within a $CD34^+$ population of cells are lineage committed, a number of researchers have used various means in an attempt to distinguish lineage committed from non-lineage committed cells. For example, Loken et al., Blood, 70:1316 (1987), used flow cytometry and a combination of light scatter and immunofluorescence staining to identify the various stages of B lymphocyte maturation. Working backward from the most mature cell to the most immature cell within a cell type, Loken, Terstappen and their colleagues showed that certain antigens are expressed on mature stages of cells but not on immature stages while different antigens may be expressed on more immature cells the expression of which then is lost as the cells mature. They also showed that cells at different levels of maturity had different light scatter properties.

In Blood, 77:1218 (1991), Terstappen et al. showed that a cell population that was $CD34^+$ and $CD38^-$ was enriched for human hematopoietic stem cells ("HSC"). HSC are defined as those cells that are capable of both limited self-renewal and differentiation into the two principle progenitor components (i.e., myeloid and lymphoid progenitors). (As used herein, "myeloid" progenitors include cells that give rise to monocytes, granulocytes and megakaryocytes but exclude cells that can-give rise to cells in the erythroid lineage. Among the "erythroid" progenitors, therefore, are only those progenitors that give rise to cells within the erythroid lineage.) Terstappen et al. demonstrated that cells within the population of cells having this phenotype were capable of limited self-renewal and differentiation into the various hematopoietic cell types. Like other researchers in the field, Terstappen et al. reported that cells of this phenotype did not express CD3, CD10, CD33 or CD71.

Following this, in co-pending and commonly assigned patent application U.S. Ser. No. 07/895,491, filed Jun. 8 , 1992, Terstappen and his co-workers described a more enriched population of human cells having the phenotype $CD34^+/CD38^-/HLA-DR^+$. They showed that this population of cells was enriched for HSC.

In addition to this work, others have examined the effects of cell adhesion molecules on HSC enriched populations. For example, Simmons et al. described the expression of VCAM-1 on certain bone marrow stromal cells as they relate to progenitor cells. See Blood, 80:388 (1992). Similarly, Ogawa, Blood, 81:2844 (1993), has described the suspected effects of different growth factors on progenitor cells.

While the work described above and in references such as Wognum et al., Blood, 76:697 (1990) and Udomsakdi et al., Blood, 80:2513 (1992), focused on the discrimination of non-lineage committed cells from lineage committed cells, on the discrimination of maturational stages within a lineage or on the use of a certain very select markers (e.g., EPO) to identify a specific progenitor lineage, there has been no careful systematic study using highly sensitive measuring means to discriminate among progenitor cells committed, specific lineage.

SUMMARY OF THE INVENTION

The present invention comprises a method to discriminate human lineage committed myeloid, lymphoid and erythroid progenitor cells. Cells that are enriched for HSC are identified using markers (e.g., monoclonal antibodies, fragments thereof, or recombinant binding proteins derived therefrom) that are specific for CD34, CD38 and HLA-DR antigens. These cells are $CD34^+/CD38^-/HLA-DR^+$. These cells also express homogeneous levels of stem cell factor receptor ("SCFR"), Leu 8 ("L-selectin"), CD18, CD33, CD44, CD48, CD49e, CD50 and CD52. Low levels of granulocyte/monocyte-colony stimulating factor receptor ("GM-CSFR"), gp130/IL-6R (gp130 signal subunit of. the interleukin-6 receptor), IL-6R and Fas Ag are expressed on cells of this phenotype, while IL-7R is not expressed at all.

Progenitor cells committed to the erythroid, myeloid or lymphoid lineages can be identified using a marker for CD34, a marker for CD38 and one or more markers that are specific for cell adhesion molecules and/or cytokine receptors that are expressed on the surface of human cells. Progenitor cells are $CD34^+/CD38^+$. Progenitor cells that are committed to the lymphoid lineage show de novo expression of IL-7R, increased expression of Fas Ag, CD49e and CD52 and decreased expression of SCFR, GM-CSFR, IL-6R, gp130/IL-6R, Leu 8, CD18, CD33, CD44 and CD50. Progenitor cells that are committed to the erythroid lineage show a complete loss of L-selectin and decreased expression of IL-6R, CD18, CD48, CD50 and CD52. Progenitor cells committed to the myeloid lineage show increased expression of GM-CSFR, IL-6R, Fas Ag, CD18, CD33, CD44, CD48 and CD49e and decreased expression of SCFR, L-Selectin and CD52.

Using this information, if one were to isolate only those cells committed to the erythroid lineage, for example, one could combine CD34, CD38 and IL-7R antibodies and look for positive expression for each marker. To look for only myeloid committed progenitor cells, one could use CD34, CD38 and IL-6R antibodies and look for positive expression of these markers. To exclude those myeloid progenitors that may be erythroid, one could select for those progenitors that are $IL-6R^+$ and $IL-7R^-$.

One means to identify and/or isolate cells of the desired lineage and/or phenotype comprises flow cytometry. Cell sorters and cells analyzers are available from a number of commercial sources, including Becton Dickinson Immunocytometry Systems ("BDIS") under the name FACS®. The general principles of flow cytometry and the use of fluorescent markers therewith is described in Herzenberg et al., Sci. Amer., 234:108 (1976). See also U.S. Pat. No. 4,727,020. In this method, monoclonal antibodies conjugated to dyes having emission spectra that are distinguishable are used. Useful dyes include r-phycoerythrin ("PE"), allophycocyanin ("APC"), fluorescein isothiocyanate ("FITC"), Texas Red (Molecular Probes), CY-5 (Biological Detection Systems), peridinin chlorophyll protein complex ("PerCP") and tandem conjugates thereof. While desired, it is not necessary that each dye have similar excitation maxima. See U.S. Pat. Nos. 4,520,110, 4,542,104, and 4,876,190.

Other means for isolating cells having the desired phenotype include columns containing a matrix of materials which will trap cells. The matrix can comprise a material which can be magnetized, such as steel wool, and used in combination with magnetic beads which are conjugated to antibodies. By serial passage of labelled cells through such a device, the desired phenotype can be achieved. Such a device is sold under the name "MACS" by Miltenyi Biotech GmbH. Alternatively, the matrix may comprise biotin and the antibodies conjugated to avidin. Again, serial passage of labelled cells would be used. Such a device is sold by CellPro, Inc. See U.S. Pat. Nos. 5,5,215,927, 5,225,353, and 5,240,856; W091/09141; and Kato et al., Cytometry, 14:384 (1993).

Human cells containing HSC can be obtained from peripheral blood, cord blood, bone marrow, thymus, spleen or liver. The source may be from an allogeneic donor or may be autologous.

Cells derived from these sources have therapeutic uses. Specifically, one or more of the desired lineages of progenitors can be isolated for transplantation into bone marrow or peripheral blood. Cells obtained from an allogeneic donor or from the patient can be obtained with or without prior mobilization of the cells while in vivo with GM-CSF or G-CSF. Having been obtained, the cells can be used immediately, expanded ex vivo through the use of growth factors such as SCF or GM-CSF, or stored for latter use. The cells can be used in a variety of circumstances. For example, in treating leukemia patients, it is important during treatment to provide platelets to prevent infection. Myeloid progenitors could be given as is or expanded to provide platelets. In HIV$^+$ patients, T cells could be given to replace depleted CD4$^+$ and/or CD8$^+$ lymphocytes.

DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION

Fetal bone marrows were obtained from aborted fetuses 16–22 weeks of gestational age and used following the guideline of the institutional review board of Stanford University Medical Center on the use of Human Subjects in Medical Research. Erythrocytes were lysed as above and the cell suspensions washed. Cells were stained first with a monoclonal antibody marker for the desired growth factor receptor or for the desired cell adhesion molecule antibody at 0.1 μg per test for 20 minutes, and then the cells were washed. Goat anti mouse Ig PE then was used as a second step reagent, and washed. After blocking with 30% mouse serum, the cells then were stained simultaneously with anti-CD34 PerCP, anti-CD38 APC and anti-HLA-DR FITC (or anti-CD71 FITC for those experiments where myeloid progenitors were distinguished from erythroid progenitors) at 0.1 μg per test for 20 minutes. The cells then were washed, and fixed in 0.5% paraformaldehyde.

All of the antibodies used herein are commercially available from one or more sources, such as BDIS, Immunotech S.A., Amac Inc., Dako, and/or have been described and clustered by the International Workshop on Human Leukocyte Antigens.

In order to identify low density antigens on human cells, a FACScan brand flow cytometer was modified so as to have three lasers illuminating the flow cell in the following sequence at intervals of 20 μseconds: 488 nm Argon laser to excite FITC and PerCP; 633 nm Helium Neon laser to excite APC; and a 532 nm YAG laser to excite PE. The latter laser excited PE so as to yield approximately 6 times higher signal to background (i.e., autofluorescence) ratio than results from excitation at 488 nm. Flow cytometric analyses were performed on the same instrument using Lysis™ 2.0 data acquisition software (BDIS) with gates set on light scattering and CD34$^+$ cells. Forward light scattering, orthogonal light scattering and three fluorescence signals were determined for each event and approximately 10,000 events were stored in listmode data files. The analysis of the listmode data files was performed with PAINT-A-GATE™ software (BDIS). (See also U.S. Pat. No. 4,845,653.) Orthogonal light scatter data was transformed by the method disclosed in U.S. Pat. No. 5,224,058.

Figure 1A:
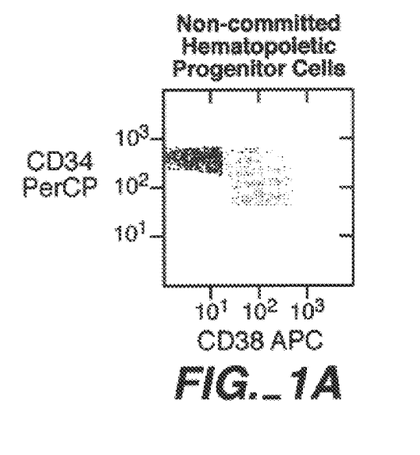
FIGS. 1A–1C comprises a series of three dot plots of fetal bone marrow cells labelled with anti-CD34 PerCP, anti-CD38 APC and anti-HLA-DR FITC wherein 1A is a plot of log PerCP versus log APC fluorescence, 1B is a plot of transformed orthogonal light scatter versus log APC fluorescence and 1C is a plot of log FITC versus log APC fluorescence.
Figure 1B:
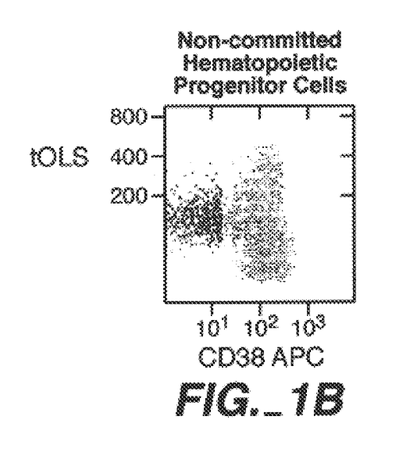
Figure 1C:
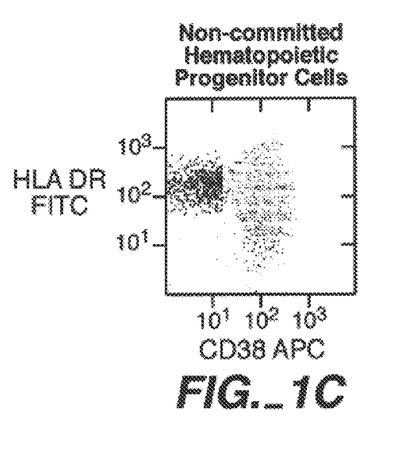

Referring to FIG. 1A, non-lineage committed human cells that enriched for HSC are shown. These cells are CD34$^+$/CD38$^-$. In FIG. 1B, these cells are shown to have low levels of orthogonal light scatter. In FIG. 1C, the expression of HLA-DR is shown. As previously described in the commonly assigned co-pending application of Terstappen et al., these cells also are HLA-DR$^+$.

In order to determine the relative levels of expression of various growth factor receptors and cell adhesion molecules on progenitor cell types, data analysis gates had to be set to define each of the three progenitor types. CD38 and transformed orthogonal light scatter were used to establish the lymphoid progenitor gate.

Figure 2A:
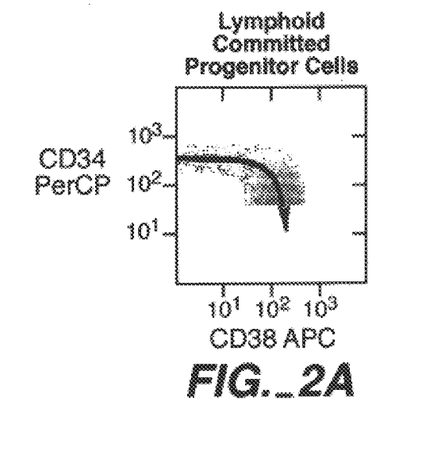
FIGS. 2A–2C comprises a series of three dot plots of fetal bone marrow cells labelled with anti-CD34 PerCP, anti-CD38 APC and anti-CD19 PE wherein 2A is a plot of log PerCP versus log APC fluorescence, 2B is a plot of transformed orthogonal light scatter versus log APC fluorescence and 2C is a plot of log PE versus log APC fluorescence. Arrows indicate direction of maturation.
Figure 2B:
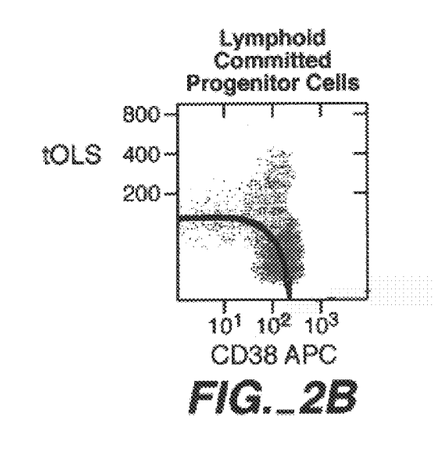
Figure 2C:
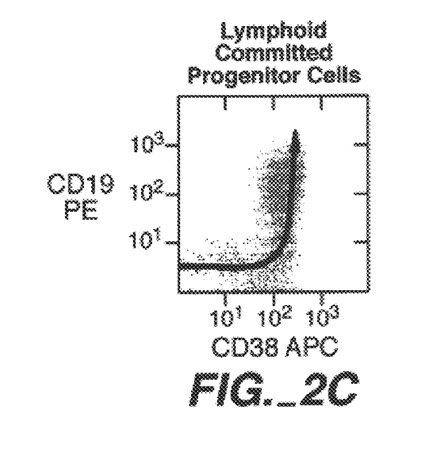
Figure 3A:
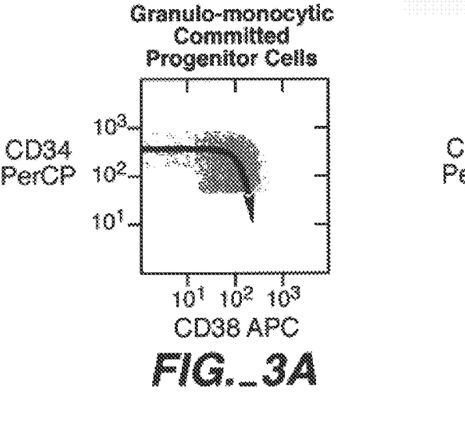
FIGS. 3A–3C comprises a series of three dot plots of fetal bone marrow cells labelled with anti-CD34 PerCP, anti-CD38 APC and anti-CD15 PE wherein 3A is a plot of log PerCP versus log APC fluorescence, 3B is a plot of transformed orthogonal light scatter versus log APC fluorescence and 3C is a plot of log PE versus log APC fluorescence. Arrows indicate direction of maturation.
Figure 3B:
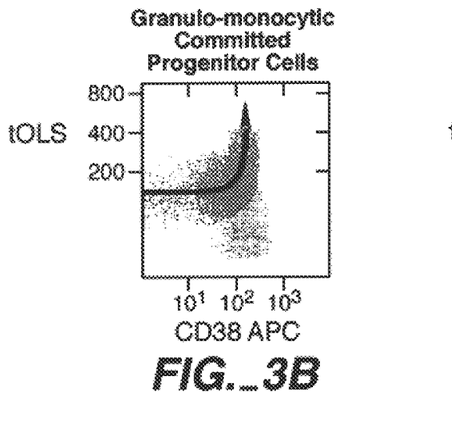
Figure 3C:
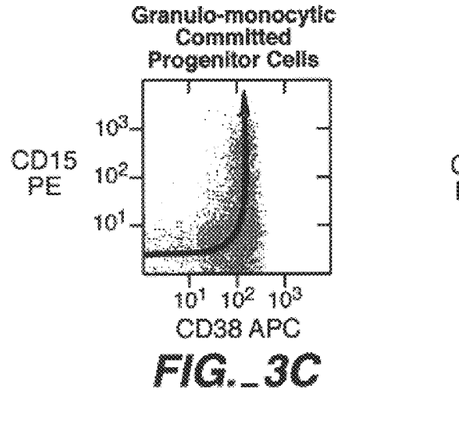

Referring to FIGS. 2–3, lymphoid and myeloid progenitors within the CD34$^+$/CD38$^+$ population of human cells were identified as follows. CD34, CD38 and CD19 or CD15 were added to fetal cells. Lymphoid cells appear in FIG. 2B having low orthogonal light scatter. Myeloid progenitors, on the other hand, have higher light scatter. Compare FIG. 3B. To confirm the validity of these gates, cells also were stained either with CD15 or CD19. Within the lymphoid gate, 94% of the cells were CD19$^+$ while CD15 did not appear to be expressed on these cells. See FIG. 2C. Within the myeloid gate, less than 7% of the cells were CD19$^+$ while 30% were CD15$^+$. See FIG. 3C.

Figure 4A:
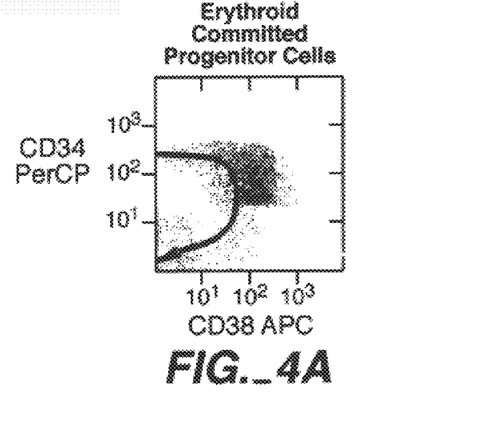
FIGS. 4A–4C comprises a series of three dot plots of fetal bone marrow cells labelled with anti-CD34 PerCP, anti-CD38 APC and anti-CD71 FITC wherein 4A is a plot of log PerCP versus log APC fluorescence, 4B is a plot of transformed orthogonal light scatter versus log APC fluorescence and 4C is a plot of log FITC versus log APC fluorescence.
Figure 4B:
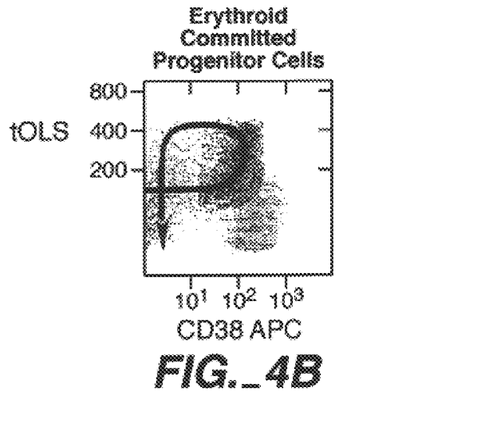
Figure 4C:
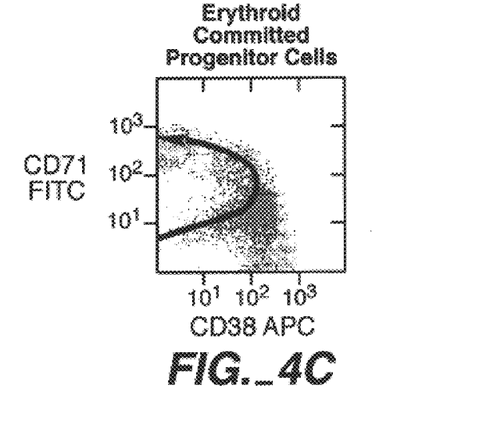

In order to identify erythroid progenitors, separate experiments were set up using CD34, CD38 and CD71. Lymphoid cells were excluded by using the lymphoid gate. Myeloid progenitors and erythroid progenitors could not be distinguished based upon CD38 versus transformed orthogonal light scatter (see FIG. 4B); however, CD71 expression splits these populations with the latter brightly expressing CD71 while the former only dimly expresses CD71. See FIG. 4C.

Figure 5A:
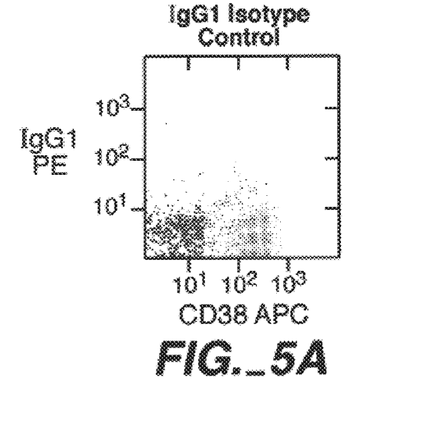
FIGS. 5A–5C comprises a series of two dot plots and one graph of fetal bone marrow cells labelled with anti-CD34 PerCP, anti-CD38 APC and an irrelevant IgG$_1$ PE wherein 5A is a plot of log PE versus log APC fluorescence, 5B is a plot of log PE fluorescence versus transformed orthogonal light scatter and 5C is a representation of log PE fluorescence as a function of maturation from non-lineage committed stage "1" cells to lymphoid ("L"), myeloid ("GM") and erythroid ("E") committed stage "2" progenitors.
Figure 5B:
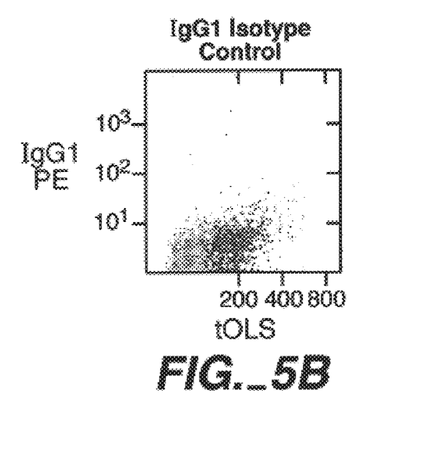
Figure 5C:
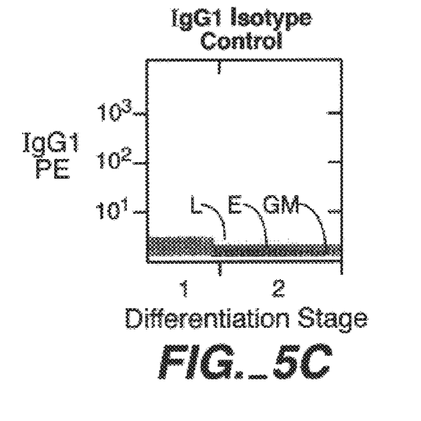
Figure 6A:
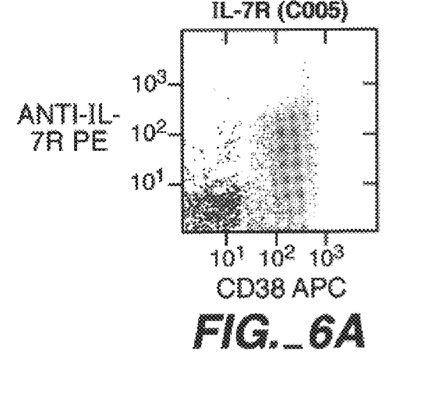
FIGS. 6A–6C comprises a series of two dot plots and one graph, as in FIG. 5, of fetal bone marrow cells labelled with anti-CD34 PerCP, anti-CD38 APC and anti-IL-7R PE.
Figure 6B:
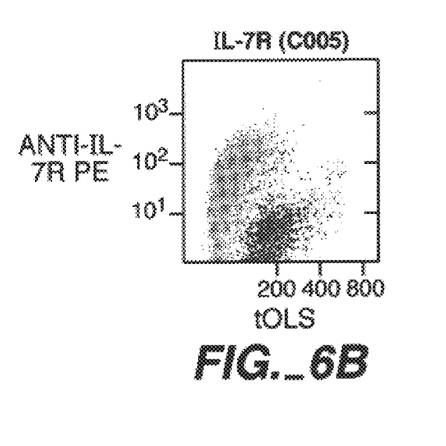
Figure 6C:
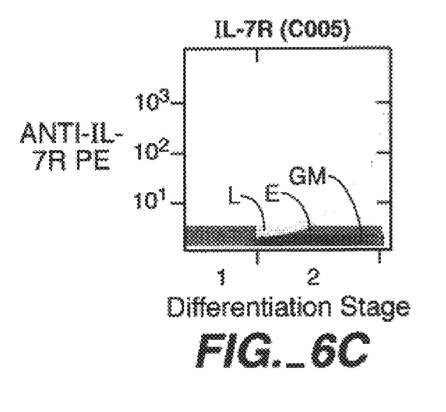
Figure 7A:
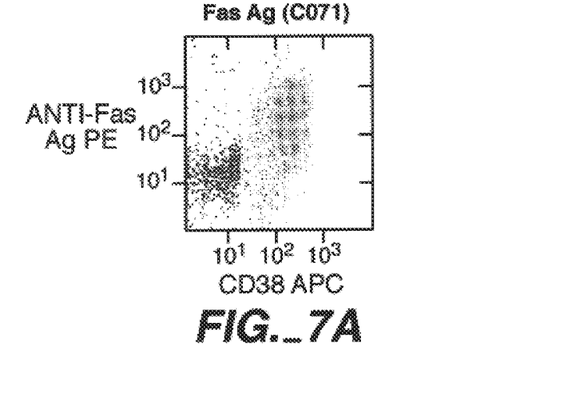
FIGS. 7A–7C comprises a series of two dot plots and one graph, as in FIG. 5, of fetal bone marrow cells labelled with anti-CD34 PerCP, anti-CD38 APC and anti-Fas Ag PE.
Figure 7B:
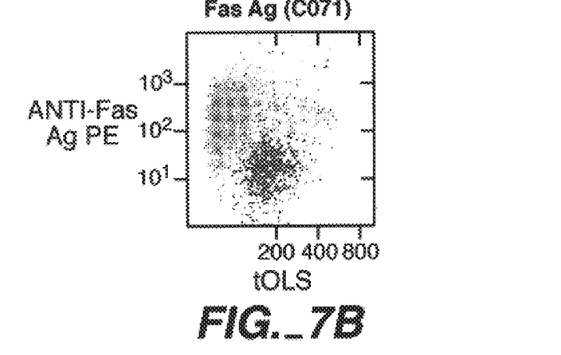
Figure 7C:
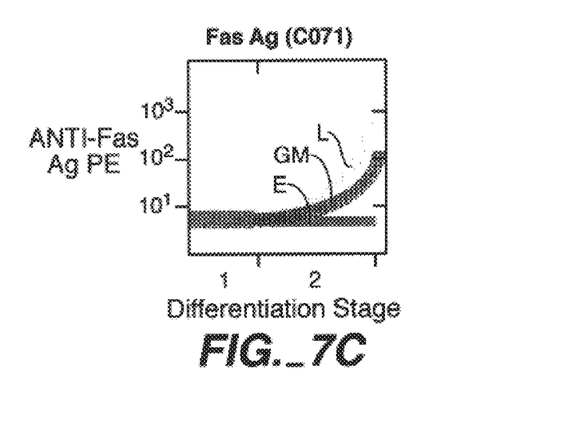
Figure 8A:
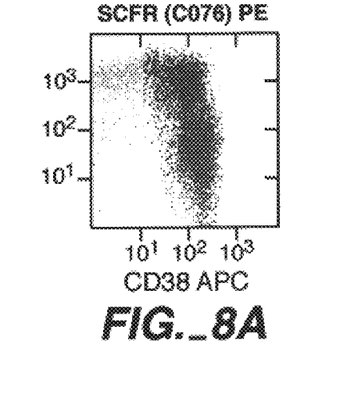
FIGS. 8A–8C comprises a series of two dot plots and one graph, as in FIG. 5, of fetal bone marrow cells labelled with anti-CD34 PerCP, anti-CD38 APC and anti-SCFR PE.
Figure 8B:
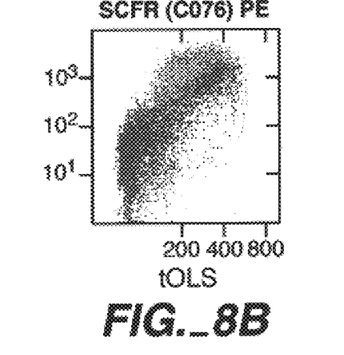
Figure 8C:
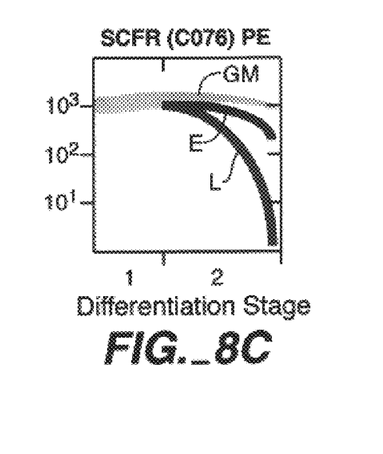
Figure 9A:
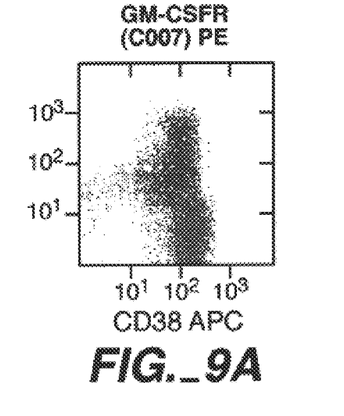
FIGS. 9A–9C comprises a series of two dot plots and one graph, as in FIG. 5, of fetal bone marrow cells labelled with anti-CD34 PerCP, anti-CD38 APC and anti-GM-CSFR PE.
Figure 9B:
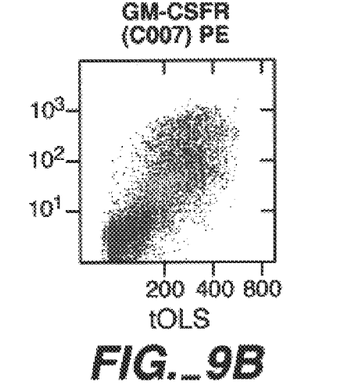
Figure 9C:
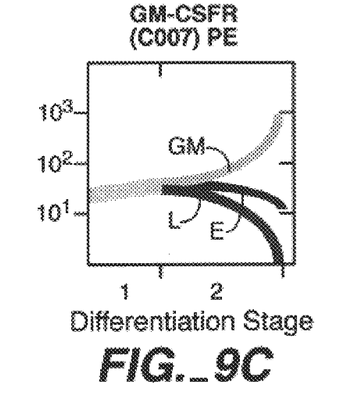
Figure 10A:
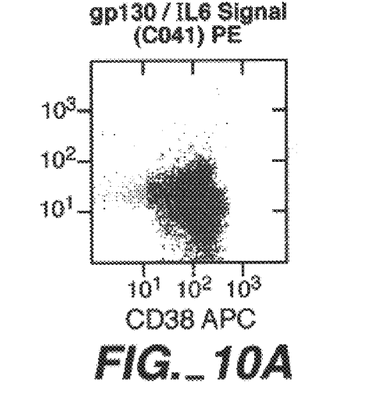
FIGS. 10A–10C comprises a series of two dot plots and one graph, as in FIG. 5, of fetal bone marrow cells labelled with anti-CD34 PerCP, anti-CD38 APC and anti-gp130/IL-6R PE.
Figure 10B:
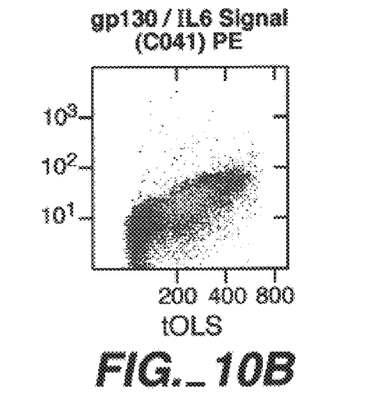
Figure 10C:
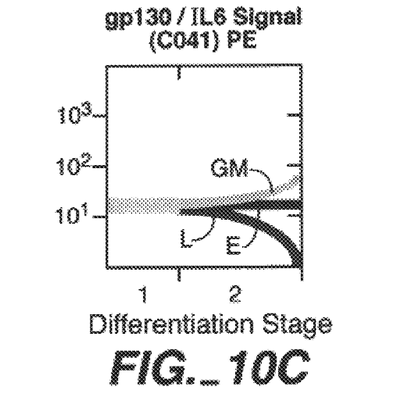
Figure 11A:
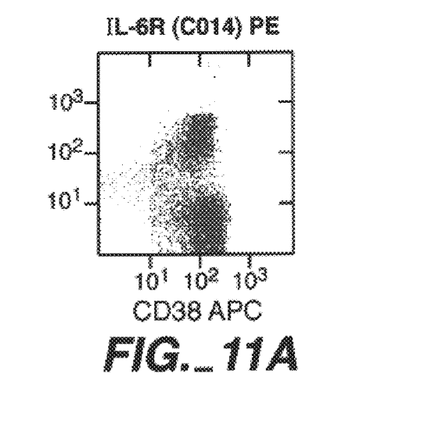
FIGS. 11A–11C comprises a series of two dot plots and one graph, as in FIG. 5, of fetal bone marrow cells labelled with anti-CD34 PerCP, anti-CD38 APC and anti-IL-6R PE.
Figure 11B:
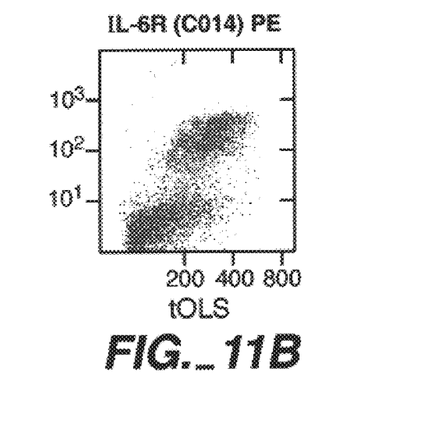
Figure 11C:
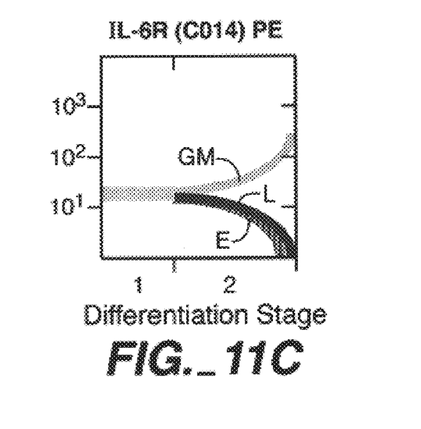
Figure 12A:
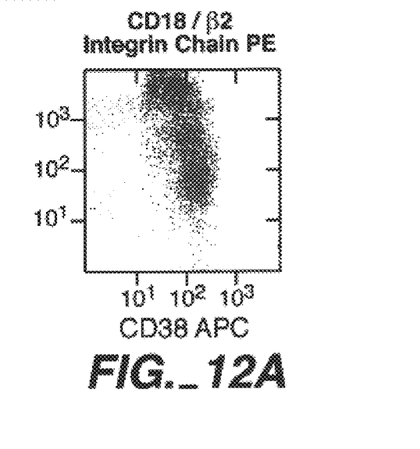
FIGS. 12A–12C comprises a series of two dot plots and one graph, as in FIG. 5, of fetal bone marrow cells labelled with anti-CD34 PerCP, anti-CD38 APC and anti-CD18 PE.
Figure 12B:
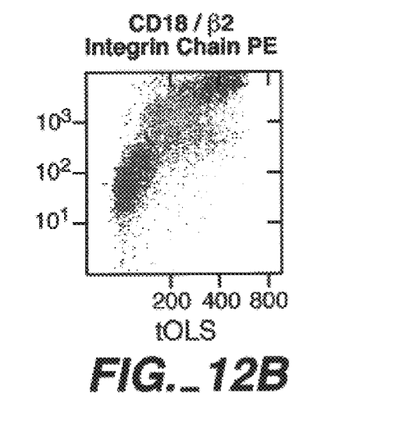
Figure 12C:
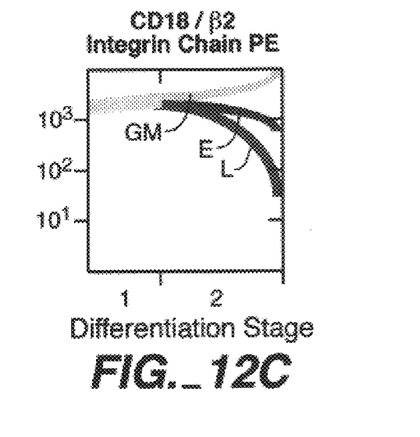
Figures 13A, 13B:
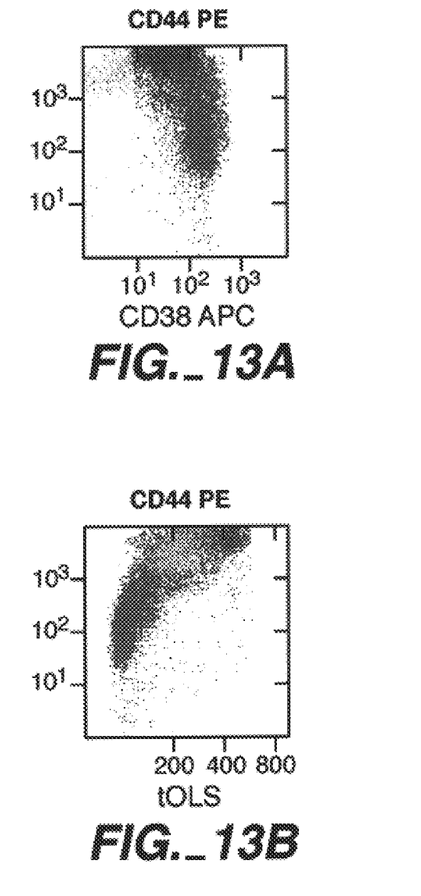
FIGS. 13A–13C comprises a series of two dot plots and one graph, as in FIG. 5, of fetal bone marrow cells labelled with anti-CD34 PerCP, anti-CD38 APC and anti-CD44 PE.
Figure 13C:
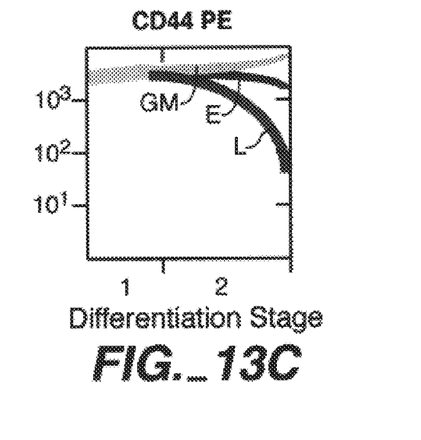
Figures 14A, 14B:
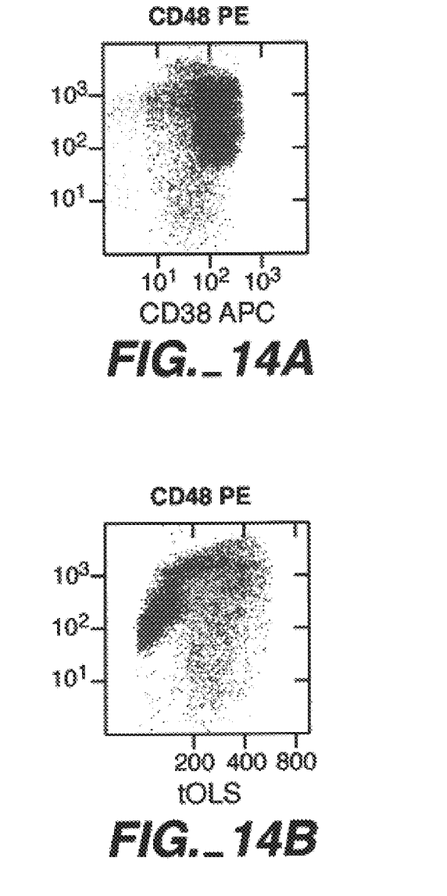
FIGS. 14A–14C comprises a series of two dot plots and one graph, as in FIG. 5, of fetal bone marrow cells labelled with anti-CD34 PerCP, anti-CD38 APC and anti-CD48 PE.
Figure 14C:
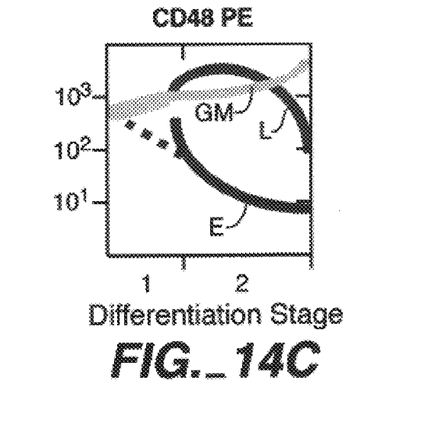
Figure 15A:
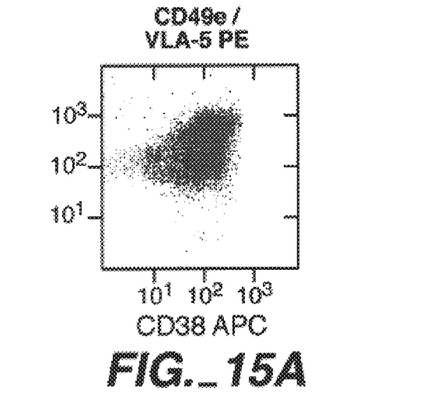
FIGS. 15A–15C comprises a series of two dot plots and one graph, as in FIG. 5, of fetal bone marrow cells labelled with anti-CD34 PerCP, anti-CD38 APC and anti-CD49e PE.
Figure 15B:
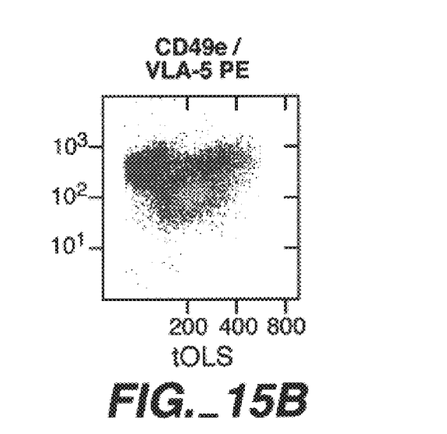
Figure 15C:
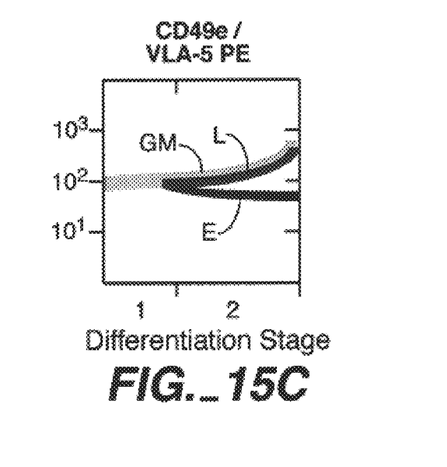
Figure 16A:
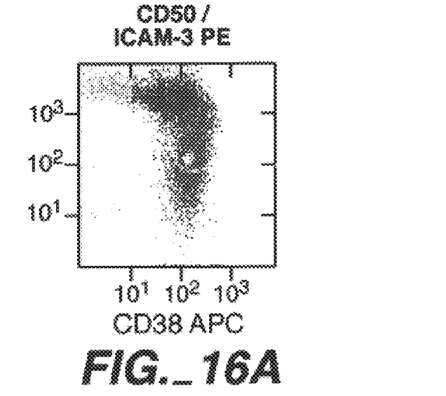
FIGS. 16A–16C comprises a series of two dot plots and one graph, in FIG. 5, of fetal bone marrow cells labelled with anti-CD34 PerCP, anti-CD38 APC and anti-CD50 PE.
Figure 16B:
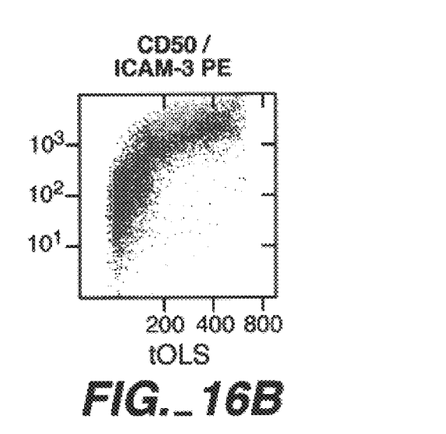
Figure 16C:
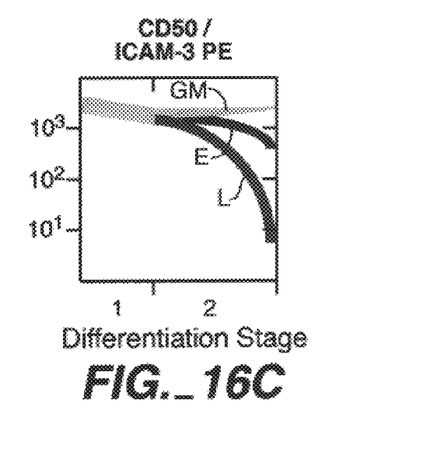
Figure 17A:
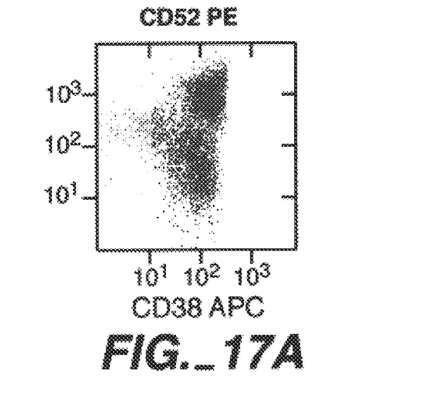
FIGS. 17A–17C comprises a series of two dot plots and one graph, as in FIG. 5, of fetal bone marrow cells labelled with anti-CD34 PerCP, anti-CD38 APC and anti-CD52 PE.
Figure 17B:
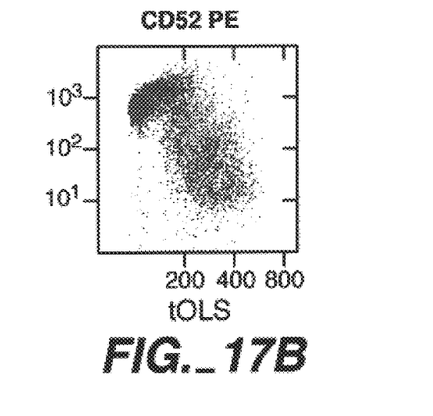
Figure 17C:
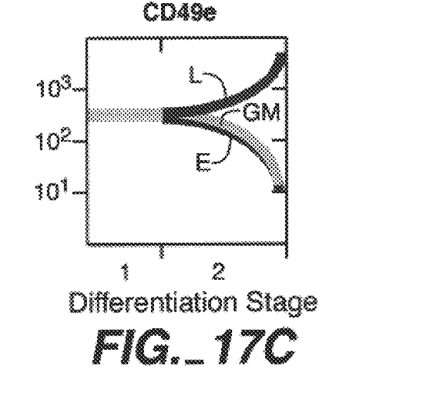
Figure 18A:
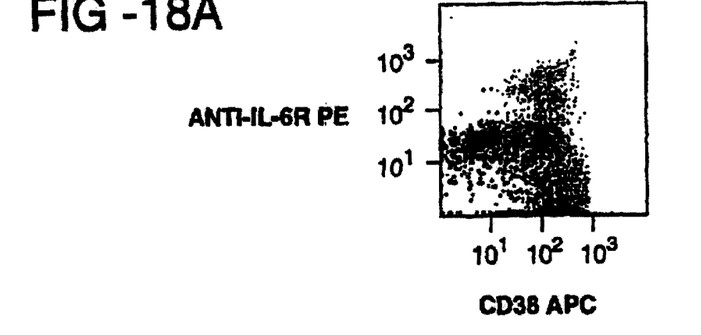
FIGS. 18A–18C comprises a series of six dot plots of fetal bone marrow cells that have been labelled with anti-CD34 Pe,rCP, anti-CD38 APC, anti-CD33 PE and anti-HLA-DR FITC wherein,18A is a plot of log PE, fluorescence versus transformed orthogonal light scatter, 18B is a plot of log PE versus log PerCP fluorescence, 18C is a plot of transformed orthogonal light scatter versus forward light scatter, 18D is a plot a log PE versus forward light scatter, 18E is a plot of log PE versus log FITC fluorescence, and 18F is a plot of log PE versus log APC fluorescence wherein CD34$^+$/CD38$^-$/HLA-DR$^+$ cells are colored green, CD34$^+$/CD38$^-$/HLA-DR$^-$ cells are colored red, myeloid committed cells are colored gray and lymphoid committed cells are colored yellow.
Figure 18B:
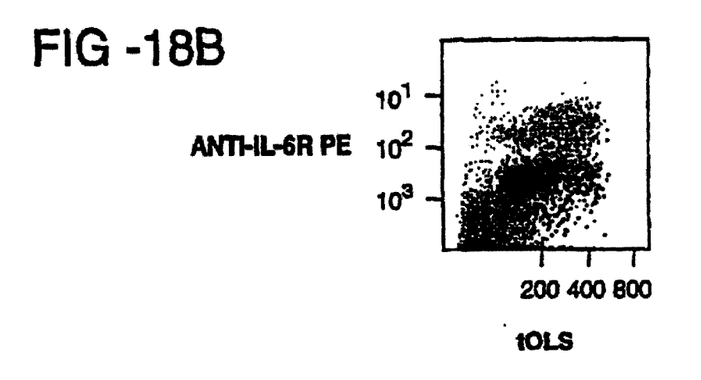
Figure 18C:
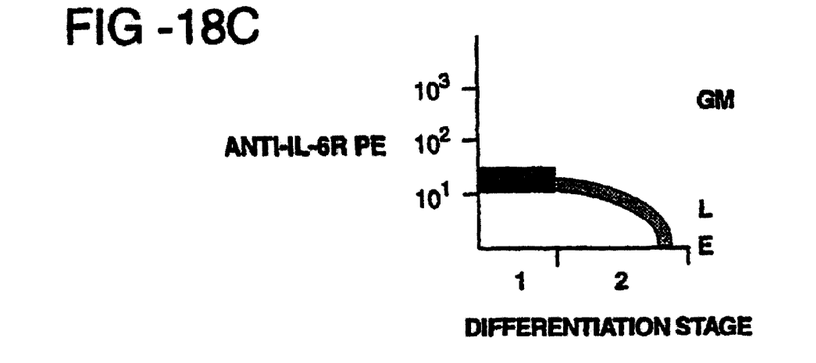
Figure 18D:
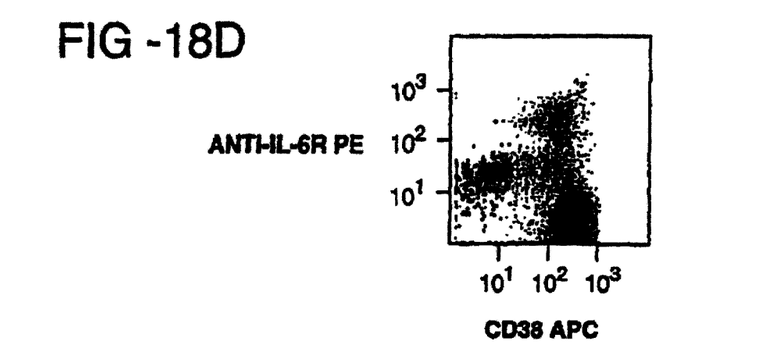
Figure 18E:
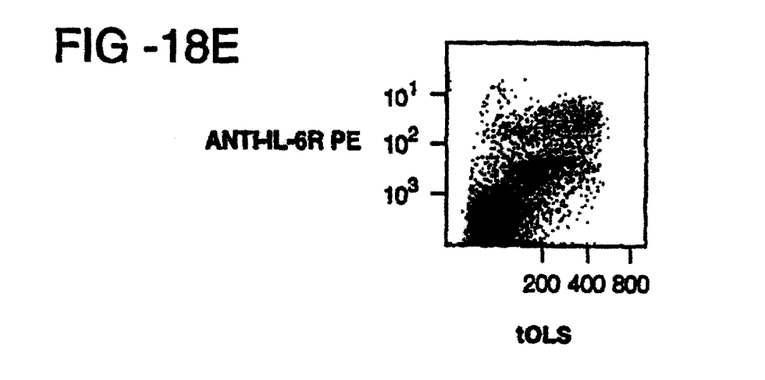
Figure 18F:
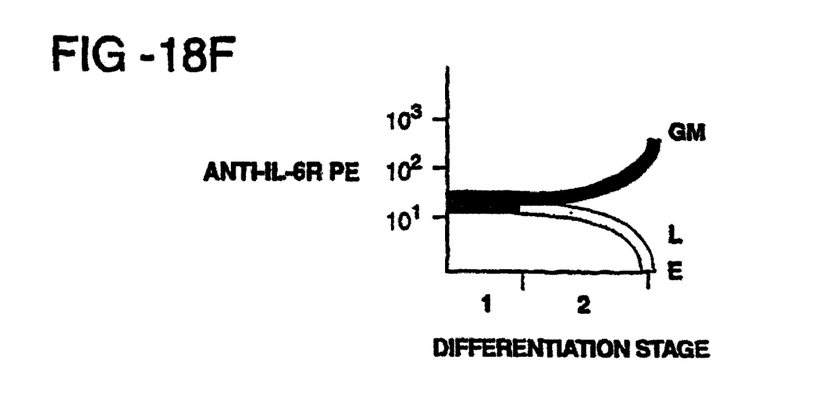

Having established gates to analyze cells from each of the three progenitor populations, human fetal cells (data shown or adult cells data not shown) were stained separately with a PE labelled isotype control, cell adhesion molecule marker or growth factor receptor marker. FIG. 5 sets forth the staining of PE versus CD38 expression (5A) and versus transformed orthogonal light scatter (5B). FIG. 5C shows the expression of PE on each of the three progenitor types as the cells progress of CD34$^+$/CD38$^-$ (i.e., stage "1") to CD34$^+$/CD38$^+$ (i.e., stage "2"). FIGS. 6–17 then set forth the results for each of the other markers used.

Of interest among these latter figures, with respect to cell adhesion molecules, is that: (1) lymphoid commitment is associated with up-regulation (or increased expression) of CD49e and CD52 and down-regulation of CD18, CD33, CD44 and CD50 (see FIGS. 12–17C, 18); (2) erythroid commitment is associated with CD18, CD48, CD50 and CD52 down-regulation; and (3) myeloid commitment is associated with increased expression of CD18, CD44, CD33, CD48, CD49e and CD50 and down-regulation of CD52. Erythroid and myeloid progenitors appear best distinguished based upon CD18 and CD48 expression.

With respect to growth factor receptors, lymphoid commitment is associated with de novo expression of IL-7R, and up-regulation of Fas Ag, and down-regulation of SCFR,GM-CSFR, IL-6R, gp130/IL/6R and IL-10R. See FIGS. 6–11C. Erythroid commitment is associated with show decreased expression of IL-6R, CD18, CD48, CD50 and CD52. Myeloid commitment is associated with increased expression of GM-CSFR, IL-6R, Fas Ag, CD18, CD44, CD48 and CD49e and decreased expression of SCFR and CD52. IL-7R expression, therefore, is useful in identifying lymphoid progenitors, while IL-6R expression appears useful in identifying myeloid progenitors. The absence of expression of both IL-7R and IL-6R appears useful in identifying erythroid progenitors.

Accordingly, methods for identifying and/or isolating progenitor cells may be accomplished by combining the expression of one or more of the cell adhesion molecules and/or growth factor receptors to isolate and identify different progenitor cell populations.

All publications and patent applications mentioned in this specification are indicative of the level of ordinary skill in the art to which this invention pertains. All publication and patent applications are herein incorporated by reference to the same extent as if each individual publication or patent application was specifically and individually indicated to be incorporated by reference.

It will be apparent to one of ordinary skill in the art that many changes and modifications can be made in the invention without departing from the spirit or scope of the appended claims.

What is claimed is:

1. A method for identifying one or more populations of human progenitor cells, said populations comprising lymphoid, erythroid and myeloid progenitors, comprising the steps of labelling a sample of human cells containing said populations with a marker for CD34, a marker for CD38 and one or more markers for cell adhesion molecules and/or growth factor receptors and identifying said populations based upon the expression of each of the markers.

2. The method of claim 1 wherein the last step of said method is carried out by means of flow cytometry.

3. The method of claim i wherein said markers comprise fluorescently labelled monoclonal antibodies.

4. The method of claim 1 wherein said growth factor receptors are selected from the group consisting of SCFR, GM-CSFR, IL-6R, gp130/IL-6R and IL-7R.

5. A method for isolating one or more populations of human progenitor cells, said populations comprising lymphoid, erythroid and myeloid progenitors, comprising the steps of labeling a sample of human cells containing said populations with a marker for CD34, a marker for CD38 and one or more markers for cell adhesion molecules and/or growth factor receptors and isolating said populations based upon the expression of each of the markers.

6. The method of claim 5 wherein the last step of said method is carried out by means of flow cytometry.

7. The method of claim 5 wherein said markers comprise fluorescently labeled monoclonal antibodies.

8. The method of claim 5 wherein said growth factor receptors are selected from the group consisting of SCFR, GM-CSFR, IL-6R, gp130/IL-6R and IL-7R.

* * * * *